United States Patent [19]
Kojima et al.

[11] Patent Number: 5,618,686
[45] Date of Patent: Apr. 8, 1997

[54] METHOD OF MEASURING THE TOTAL KETONE BODY AND A SAMPLE REAGENT

[75] Inventors: Ryo Kojima; Yoshiro Sato; Akiko Takekawa; Katsuhiro Katayama, all of Fukushima-ken, Japan

[73] Assignee: Nitto Boseki Co., Ltd., Fukushima-ken, Japan

[21] Appl. No.: 205,797

[22] Filed: Mar. 4, 1994

[30] Foreign Application Priority Data

Mar. 8, 1993 [JP] Japan .................................. 5-046628

[51] Int. Cl.$^6$ .............................. C12Q 1/32; C12Q 1/26; G01N 33/53; G01N 31/00
[52] U.S. Cl. .............................. 435/26; 435/25; 435/14; 435/4; 435/148; 435/975; 436/14; 436/63; 436/74; 436/43
[58] Field of Search .................. 435/26, 25, 14, 435/4, 148, 975; 436/130, 128, 127, 14, 63, 74, 43

[56] References Cited

U.S. PATENT DOCUMENTS

| | | | |
|---|---|---|---|
| 3,862,012 | 1/1975 | Stork | 435/26 |
| 3,964,974 | 6/1976 | Banauch et al. | 435/26 |
| 4,019,961 | 4/1977 | Klose et al. | 435/26 |
| 4,132,768 | 1/1979 | Vi et al. | 436/130 |
| 4,517,301 | 5/1985 | Greene | 436/128 |
| 4,529,704 | 7/1985 | Trimmer et al. | 436/128 |
| 4,742,001 | 5/1988 | Marui et al. | 435/26 |
| 4,803,158 | 2/1989 | Shigeta et al. | 435/26 |
| 5,204,267 | 4/1993 | Sangha et al. | 436/95 |

FOREIGN PATENT DOCUMENTS

| | | |
|---|---|---|
| 35232/80 | 12/1980 | Japan . |
| 158799/92 | 1/1992 | Japan . |

OTHER PUBLICATIONS

Williamson et al., 1962, "Enzymic Determination of D(–)-β-Hydroxybutyric Acid and Acetoacetic Acid in Blood," *Biochem. J.*, 82:90–96.

Harano et al., 1985, "Direct automated assay method for serum or urine levels of ketone bodies," *Clinica Chimica Acta*, 151:177–183.

Uno et al., 1987, "A simple and sensitive assay for blood ketone bodies using highly purified 3-hydroxybutyrate dehydrogenase," *Clinica Chimica Acta*, 168:253–255.

Harano et al., 1990, "Development of Stable Film Test for Rapid Estimation of Blood or Plasma 3-Hydroxybutyrate," *Diabetes Care*, 13(5):522–524.

Harano et al., 1983, "Sensitive and simplified method for the differential determination of serum levels of ketone bodies," *Clinica Chimica Acta*, 134:327–336.

Eriksson, 1972, "Micro Method for Determination of Ketone Bodies by Head–Space Gas Chromatography," *Analytic Biochemistry*, 47:235–243.

*Primary Examiner*—John Kight
*Assistant Examiner*—Louise Leary
*Attorney, Agent, or Firm*—Banner & Witcoff, Ltd.

[57] ABSTRACT

A method of measuring the total ketone body in a sample comprising converting acetoacetic acid in the sample to 3-hydroxybutyric acid in advance and subsequently converting the whole 3-hydroxybutyric acid including 3-hydroxybutyric acid existing in the sample originally to acetoacetic acid to lead the reduction of nicotinamide adenine dinucleotide according to the action of 3-hydroxybutyrate dehydrogenase and a sample reagent thereof is disclosed. According to this invention an assay of the total ketone body in samples can be carried out conveniently, highly precisely and quickly.

6 Claims, 5 Drawing Sheets

REACTION TIME COURSE IN THE CALIBRATION CURVE OF 3-HYDROXYBUTYRIC ACID

METHOD OF MEASURING THE TOTAL KETONE BODY AND A SAMPLE REAGENT

FIELD OF INVENTION

The present invention relates to a method of assaying the total ketone body in a sample, and more specifically, relates to a method of measuring the total amount of acetoacetic acid and 3-hydroxybutyric acid in body fluid, particularly in blood serum, blood plasma or urine (hereinafter referred to as the total ketone body), which is known as a diagnosis marker of diabetes in the field of clinical tests, and test reagents for the assay. The present invention provides a simple and highly precise assay method using an enzyme, and test reagents for carrying out the assay.

PRIOR ART

When saccharometabolism is due to lack of supply of carbohydrate or an impediment in its utilization, stress, an excess of exercise on diabetes, fat metabolism accelerates substitutionally, and a large amount of a fatty acid is released from adipose tissue. It is known that the released fatty acid is beta-oxidized at a hepatic mitochondria and that as a result the amount of acetoacetic acid and 3-hydroxybutyric acid in body fluid increases. It is useful particularly for diagnosing diabetes to assay these compounds, and is deemed to be extremely useful clinically (Yukio Shigeta: Keton Body, Nihon Rinsho, 40, autumn special issue, 250 (1982)).

As a method of assaying a ketone body, the following have been reported:

(1) according to gas chromatography (refer to Analgt. Biochem., 47, 235 (1972); hereinafter referred to as GC);

(2) a semi-quantitative method utilizing the coloration of acetone and acetoacetic acid by nitroprusside (hereinafter referred to as a semi-quantitative method);

(3) a method of subjecting acetoacetic acid to a color reaction by coupling it with diazonium salt of p-nitrophenyldiazonium fluoroborate and subjecting it to colorimetry (refer to Japanese Patent Public Disclosure No. 15004/1980); or a modification thereof, a method comprising reacting acetoacetic acid with p-nitrophenyldiazonium fluoroborate in the presence of a surface active agent, alkalizing it to form a stable azo compound and subjecting it to colorimetry (refer to Japanese Patent Public Disclosure No. 5959/1984; hereinafter referred to colorimetry);

(4) an enzyme method using 3-hydroxybutyric acid dehydrogenated enzyme (refer to Yukio Shigeta: Nihon Rinsho, 38, 638 (1980), and Williamson D. H.: Biochem. J. 82, 90–96 (1962); hereinafter referred to as an enzyme method); and (5) a method utilizing an enzyme cycling reaction according to 3-hydroxybutyric acid dehydrogenated enzyme (refer to Japanese Patent Public Disclosure No. 158779/1992; hereinafter referred to an enzyme cycling method).

Samples for the measurement of a ketone body are human body fluid, particularly blood serum or blood plasma of diabetic patients. A ketone body is a general term for acetoacetic acid and 3-hydroxybutyric acid; generally 3-hydroxybutyric acid occupies a higher concentration than acetoacetic acid and the difference tends to become large at sick conditions. Since acetone easily gasifies, is unstable and exhausted through expiration, it is not often assayed generally.

Hence, the ketone body according to the present invention means "a combination of acetoacetic acid and 3-hydroxybutyric acid".

Problems of conventional methods of assaying the ketone body are as follows.

The GC method is a method comprising chemically converting acetoacetic acid and 3-hydroxybutyric acid to acetone and measuring the acetone. Pretreatment of a sample is essential in a method which gives rise to problems in treating a large number of samples in a short time.

The semi-quantitative method is useful for providing an index for urgent treatment such as an intake of carbohydrate and the administration of insulin. However, since the method functions on the basis of detection of the active hydrogen of a molecule, it is disturbed by a compound having active hydrogen present in a sample, and further it has an essential defect that 3-hydroxybutyric acid having no active hydrogen cannot be detected. In addition, it has such a low sensitivity that only acetoacetic acid of more than 0.5 mM and acetone of more than 2 mM can be detected, and hence it is impossible around normal values to determine a disease state.

Though colorimetry is excellent in terms of its high sensitivity and capability of carrying out an assay in a short time, it is necessary in advance of a measuring step to subject a sample to a deproteinizing treatment or dialysis. Hence, it is not suitable for application to an automatic analyzer for measurement of many samples at one time.

An enzyme method gives rise to no special problem for the measurement of 3-hydroxybutyric acid. In the case of measuring acetoacetic acid, however, it has a defect that since the consumption of reduced-type nicotinamide adenine dinucleotide (reduced-type NAD) is measured, a slight absorbance decrease is measured in the high absorbance range, and hence that measurement precision is sacrificed.

An enzyme cycling method has advantages such that its sensitivity is extremely high and that no pretreatment of a specimen is needed, and that it can be easily applied to an automatic analyzer for measuring many samples at one time. However, since the as say employs thionicotinamide adenine dinucleotide (thio NAD) which is difficult to function as a coenzyme of 3-hydroxybutyrate dehydrogenase, an unusually high concentration of 3-hydroxybutyrate dehydrogenase is required. Hence, this method is uneconomical. In addition, since the maximum absorption wavelength of the reduced-type thio NAD, an analogue of NAD, is around 400 nm and measurement is performed at that wavelength, it is prone to be affected by hemolysis and the presence of bilirubin.

SUMMARY OF THE INVENTION

The object of the present invention is to provide a convenient and rapid method of assaying a ketone body in a sample. The method can be performed with high precision, and requires no pretreatment of the specimen. Thus it solves the defects of conventional methods of measuring a ketone body as described above, and moreover provides a method of measurement by means of a general-purpose automatic analyzing device and a reagent therefor.

The present invention relates to a method of assaying the total ketone body in a sample, which comprises the steps of:

(1) converting acetoacetic acid in the sample to 3-hydroxybutyric acid;

(2) converting both 3-hydroxybutyric acid originally existed in the sample and 3-hydroxybutyric acid converted by step (1) to acetoacetic acid with the aid of 3-hydroxybutyrate dehydrogenase and nicotinamide adenine dinucleotide, and (3) measuring the amount of reduced-type nicotinamide adenine dinucleotide formed by step (2). This method is characterized by converting acetoacetic acid in a sample into 3-hydroxybutyric acid prior to the reduction reaction.

Moreover, the present invention relates to diagnostic reagents for assaying the total ketone body, which comprises (1) a buffering agent, (2) 3-hydroxybutyrate dehydrogenase (EC1.1.1.30), (3) reduced-type nicotinamide adenine dinucleotide and oxidized-type nicotinamide adenine dinucleotide, (4) an enzyme capable of converting oxidized-type nicotinamide adenine dinucleotide to reduced-type nicotinamide adenine dinucleotide according to the conjugation reaction with 3-hydroxybutyrate dehydrogenase (EC1.1.1.30), (5) a substrate for the enzyme of (4), and (6) an inhibitor of the enzyme of (4).

DETAILED DESCRIPTION

Figure 1:
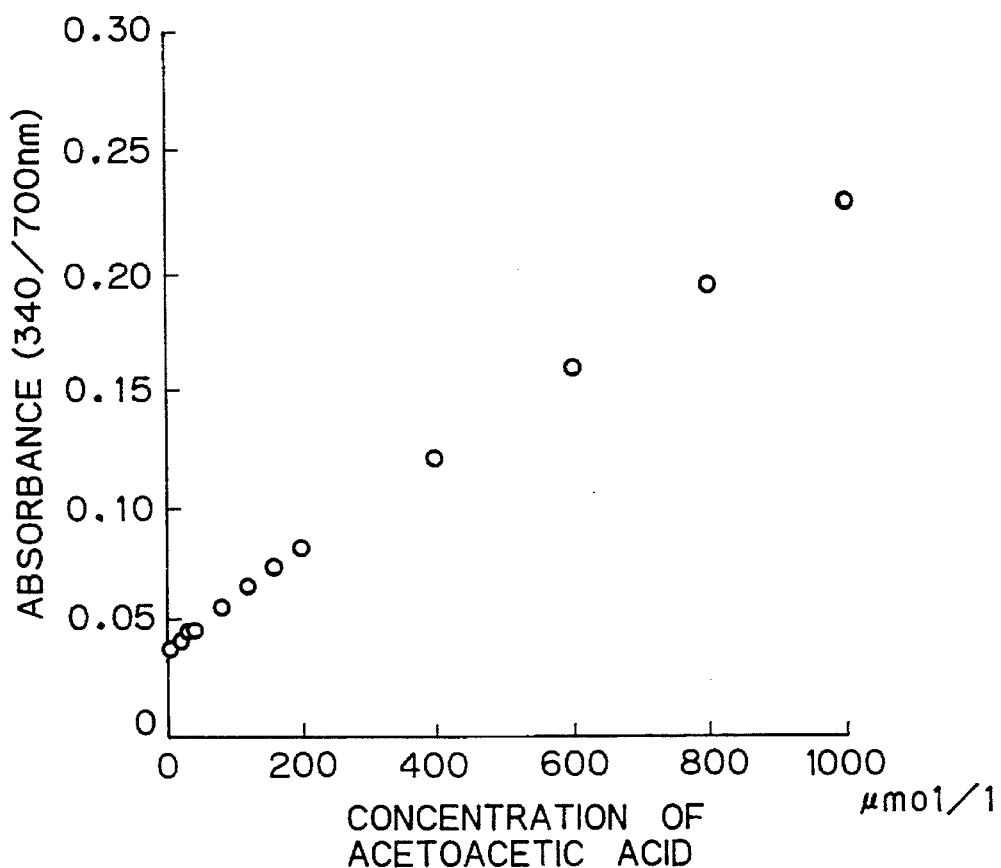
FIG. 1 shows a calibration curve of acetoacetic acid.

The enzyme method of assaying acetoacetic acid and 3-hydroxybutyric acid in a sample utilizes the following reaction:

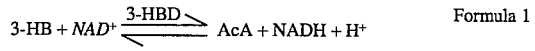

3-HB : 3-hydroxbutryic acid

AcA : acetoacetic acid

3-HBD : 3-hydrocybutric deydrogenase $NAD^+$: oxidized-type nictotinamide adenine dinucleotide NADH: reduced-type nicotinamide adenine dinucleotide The method of determining 3-HB based on the present reaction is to measure the ultraviolet absorption of NADH to be formed, and if a sufficient amount of a sample is taken, a satisfactory measuring precision is shown even at a normal region (59±33 μM: Nihon Rinsho, 40, autumn special issue, 250 (1982)). With respect to AcA measurement based on the present reaction, however, it is determined indirectly by measuring NADH to be consumed, and in case of measuring a low concentration of sample at a region with a high absorbance (high-concentration NADH region) established to have a sufficient range of measurement, the measuring precision is reduced due to the measurement of a slight decrease of absorbance (Nobuo Sakamoto: Sogo Rinsho, 40, 1359–64 (1991)).

We have noted the advantage in the method of measuring 3-HB, namely, the point that a nearly satisfactory measurement precision is shown in the case of measuring the absorbance of NADH to be formed at a region with a low absorbance (low-concentration NADH region) for determination, and further have made assiduous studies, taking an inhibitory reaction due to lactate dehydrogenase, measures against the affection of other coexisting materials at the time of measurement and the stabilization of a reagent into consideration, and as a result have completed the present invention.

In the case of converting AcA in a sample to 3-HB according to the reaction of the formula 1, the reaction is proceeded and finally finished while NADH is being consumed quantitatively. In this case, in order to measure AcA with a high concentration, an amount of NADH corresponding the consumption must be added to the reaction system. In the case of allowing a sufficient amount of NADH to exist, however, an initial absorbance must be high. In such a condition, a slight absorbance change to be obtained by the reaction of a sample with such a low concentration such as found in a normal region cannot be measured precisely because it is hidden by the noise of the initial absorbance (high absorbance). The present inventors while investigating this problem have found that AcA can be converted to 3-HB by adjusting the concentration of reduced-type nicotinamide adenine dinucleotide (NADH) to be added to 0.2 mM or less, preferably to a concentration of 0.01 to 0.10 mM, and further by conjugating another enzyme reaction forming NADH using oxidized-type nicotinamide adenine dinucleotide ($NAD^+$) as a coenzyme (for example, isocitrate dehydrogenase (EC1.1.1.41), which maintaining the initial absorbance at a low level. That is, by using NADH with a low concentration, AcA can be converted to 3-HB completely while NADH is supplied in the conjugation enzyme reaction. Subsequently, an excess amount of NAD is added therein and further a reaction pH is shifted to an alkaline region to completely convert both 3-HB existing in the sample from the beginning and 3-HB converted from AcA to AcA. The present inventors have found that, at this time, AcA in the sample can be measured together with 3-HB with good precision by measuring the absorbance of NADH formed according to the reaction. Besides, by conjugating a NADH-forming enzyme reaction, the added reduced-type nicotinamide adenine dinucleotide can exist stably without any denaturation or deterioration even at a weak alkaline region, such as a pH of from about 7 to about 7.5. Moreover, by conjugating lactate dehydrogenase, the error in the measurement of a sample containing a high concentration of lactate dehydrogenase which has long been a problem can be solved completely.

According to the method of measuring the total ketone body in a sample of the present invention, absorbance is measured by means of a spectrophotometer after a two step reaction. AcA in the sample is completely converted to 3-HB in the first-step by the action of 3-HBD in the presence of NADH the concentration of which is controlled at a low level. NADH which has been consumed at this step is compensated to an initial level (a level not becoming a high concentration) in a short time by conjugating another enzyme reaction (for example, using isocitrate dehydrogenase (EC1.1.1.41)) Forming NADH even when a high concentration of AcA is reacted. Also in this first step reaction, pyruvic acid in the sample is quickly converted to lactic acid with the aid of lactate dehydrogenase added, and NADH which is consumed at this time is compensated to an initial level in a short time by conjugating another enzyme reaction forming NADH in the same manner as AcA is reacted. In the second-step, the reaction for converting 3-HB to AcA is started by adding an excess amount of NAD and by shifting a reaction pH to an alkaline region. At the same time, an inhibitor of the enzyme reaction which formed NADH in the first step is added to the reaction system and further a known inhibitor of lactate dehydrogenase is added to stop the second step of the reaction, so that AcA in the sample is converted to 3-HB and at the same time the NADH formation reaction is led to exactly proceed and the amount of formed NADH is measured in terms of the increase of absorbance (refer to Examples 1 and 2).

As described above, the concentration of NADH in the first-step is controlled to a low level, namely, a low absorbance, and at the same time, in the second step of the reaction, the concentration of the total ketone body can be measured in terms of the increase of absorbance according to the NADH formation reaction associated with the conversion of AcA to 3-HB. According to the above method, the highly accurate measurement of the total ketone body has become possible by means of an automatic analyzer. In addition, according to the conjugation of another NADH forming enzyme reaction, the stabilization of NADH could be performed, and further according to the conjugation of a lactate dehydrogenase reaction, the error in the measurement of a sample containing lactate dehydrogenase in a high level can be completely solved (refer to Example 5).

Lactate dehydrogenase is added in order to convert pyruvic acid in a sample to lactic acid. If pyruvic acid exists in the sample, NADH is converted to $NAD^+$ when lactic acid will be formed according to a reverse reaction by the action of lactate dehydrogenase, and hence NADH formed in the main reaction decreases and the error of measurement occurs. This phenomenon is more remarkable in samples containing a higher concentration of lactate dehydrogenase, and prevents accurate measurement of the ketone body.

In the present invention, pyruvic acid in a sample is previously converted to lactic acid with the aid of NADH and a lactate dehydrogenase to remove problems caused by pyruvic acid. Subsequently, an inhibitor of lactate dehydrogenase is used in the second step of the reaction to prevent the reverse reaction, in which the conversion of lactic acid to pyruvic acid will occur.

The reaction mechanism of the method of assay according to the present invention can be represented by the following formulae. Incidentally, preferable examples of reagents are used here.

Formula 2

First step of the reaction (AcA → 3-HB)

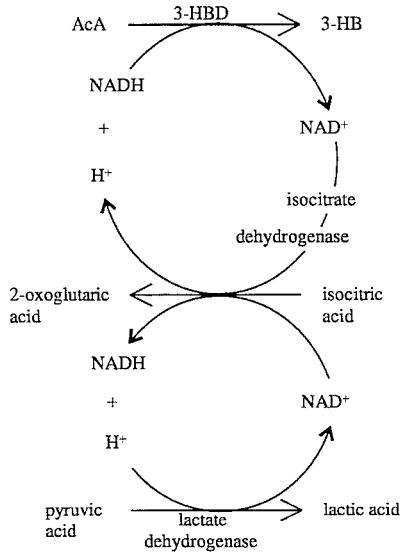

Formula 3

Second step of the reaction (3-HB → AcA & measurement of absorbance rise)

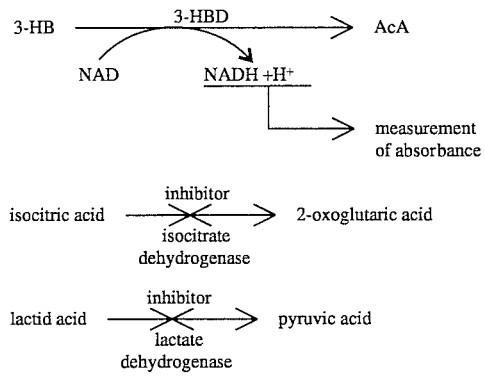

Enzymes which can be used in the conjugation reaction with 3-HBD (and lactate dehydrogenase) at the above first step of the reaction in the present invention are as follows in addition to the above-mentioned isocitrate dehydrogenase reaction.

Alcohol dehydrogenase (EC1.1.1.1)

Glucose-6-phosphate dehydrogenase (EC1.1.1.49)

Aldehyde dehydrogenase (EC1.2.1.5) and (EC1.2.1.3)

Glucose dehydrogenase (EC1.1.1.47) and (EC1.1.1.119)

The most preferable enzyme to be used in the conjugation reaction in practice is isocitrate dehydrogenase.

Regarding the use of each enzyme, substrates which do not inhibit the desired reaction and the measurement of absorbance according to the present invention can be used.

As an enzyme inhibitor useful to the second step of the reaction the followings can be used.

To isocitrate dehydrogenase can be used conventional chelating agents, for example, EDTA and trans-1,2-cyclohexanediamine-N,N,N',N'-acetic acid.

Examples of the inhibitor to the lactate dehydrogenase include oxalic acid and oxamic acid.

Although the pH of the first step of the reaction according to the present invention varies depending on the kinds of conjugation enzymes to be used; it is generally at a pH of 7.0 to 7.5, preferably of 7.3 to 7.5. The second step of the reaction is carried out generally at a pH of 8.0 to 9.0, preferably of 8.7 to 8.9.

The present invention will be illustrated in more detail and specifically by the following Examples.

EXAMPLE 1

Calibration Curve in the Measurement of the Total Ketone Body

Figure 2:
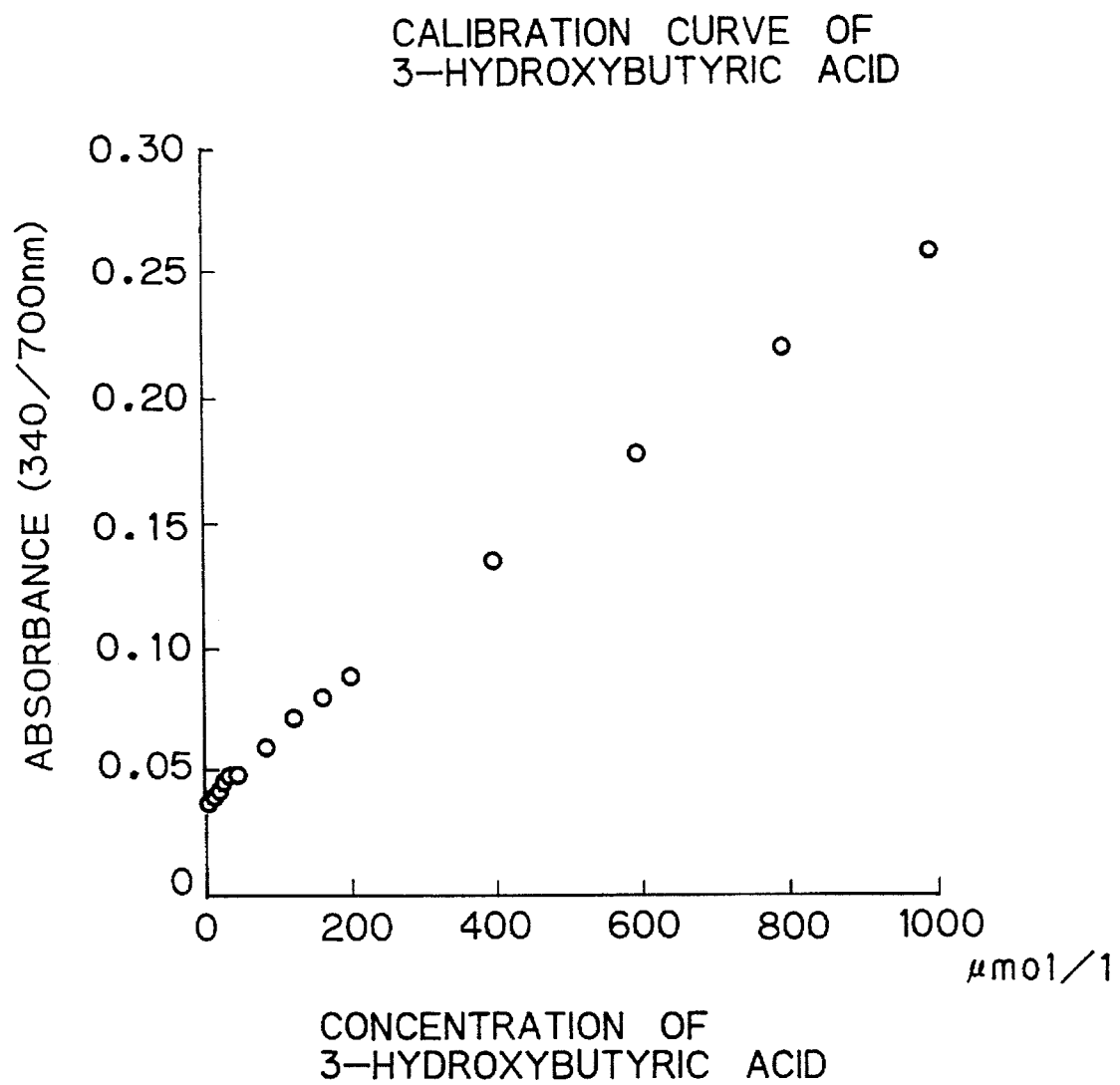
FIG. 2 shows a calibration curve of 3-hydroxybutyric acid.

Calibration curves which were obtained when AcA and 3-HB at a concentration of 0 to 1000 μmol/l are reacted according to the method of the present invention are shown in FIG. 1 (calibration curve of AcA) and FIG. 2 (Calibration curve of 3-HB). The used reaction conditions are as follows.

AcA and 3-HB at each of the indicated concentrations were used as samples, and each of the samples (20 μl) were reacted with 240μl of the first reagent and 60 μl of the second reagent having the following compositions. Then, the change of absorbance was measured at points of 24 to 50 at a primary wavelength of 340 nm and a secondary wavelength of 700 nm by means of an automatic analyzer (Hitachi Model 7150).

| First Reagent | |
|---|---|
| Toris (hydroxymethyl) aminomethane | 80 mM |
| NaCl | 60 mM |
| Magnesium acetate *1 | 10 mM |
| DL-isocitric acid | 2 mM |
| Reduced-type nicotinamide adenine dinucleotide | 0.05 mM |
| Adenosine-5'-monophosphate *2 | 1 mM |
| isocitrate dehydrogenase | 1000 U/l |
| 3-hydroxybutyrate dehydrogenase | 2000 U/l |
| lactate dehydrogenase | 1000 U/l |
| pH: 7.40 | |
| Second Reagent | |
| Toris (hydroxymethyl) aminomethane | 500 mM |
| NaCl | 150 mM |
| Trans-1,2-cyclohexanediamine-N,N,N',N'-tetraacetic acid | 50 mM |
| Oxalic acid | 200 mM |
| Oxidized-type nicotinamide adenine dinucleotide | 5 mM |
| pH: 8.80 | |

*1: A source of $Mg^{2+}$ which is a cofactor for activating isocitrate dehydrogenase
*2: A cofactor for activating isocitrate dehydrogenase AcA was measured in terms of the reaction producing reduced-type nicotinamide adenine dinucleotide, and excellent straight line was shown over a range from a low concentration to a high concentration as similar to the calibration curve of 3-HB.

EXAMPLE 2

Reaction Time Course in the Measurement of the Total Ketone Body

Figure 3:
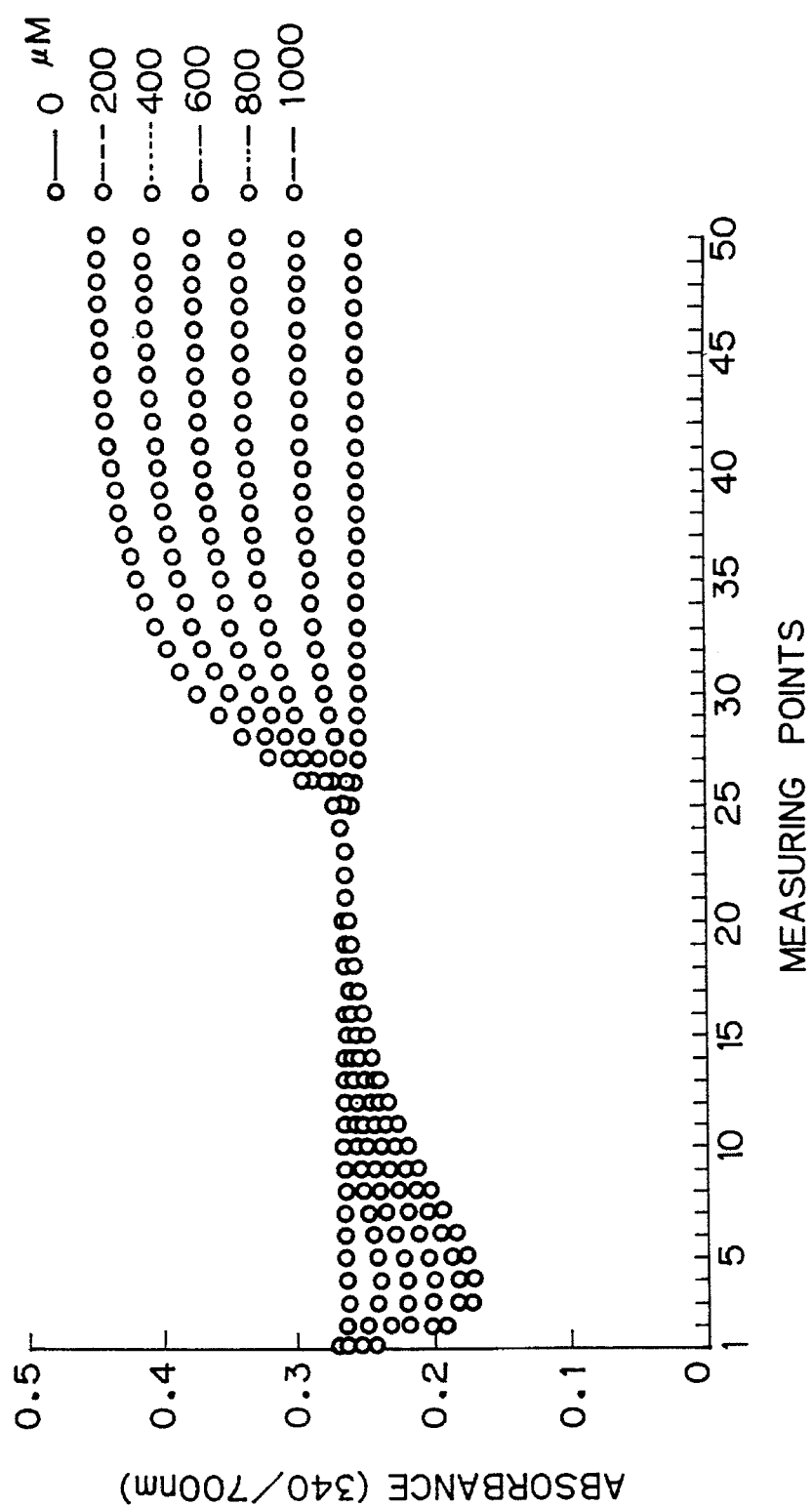
FIG. 3 is a graph showing reaction time courses in the calibration curve of acetoacetic acid.
Figure 4:
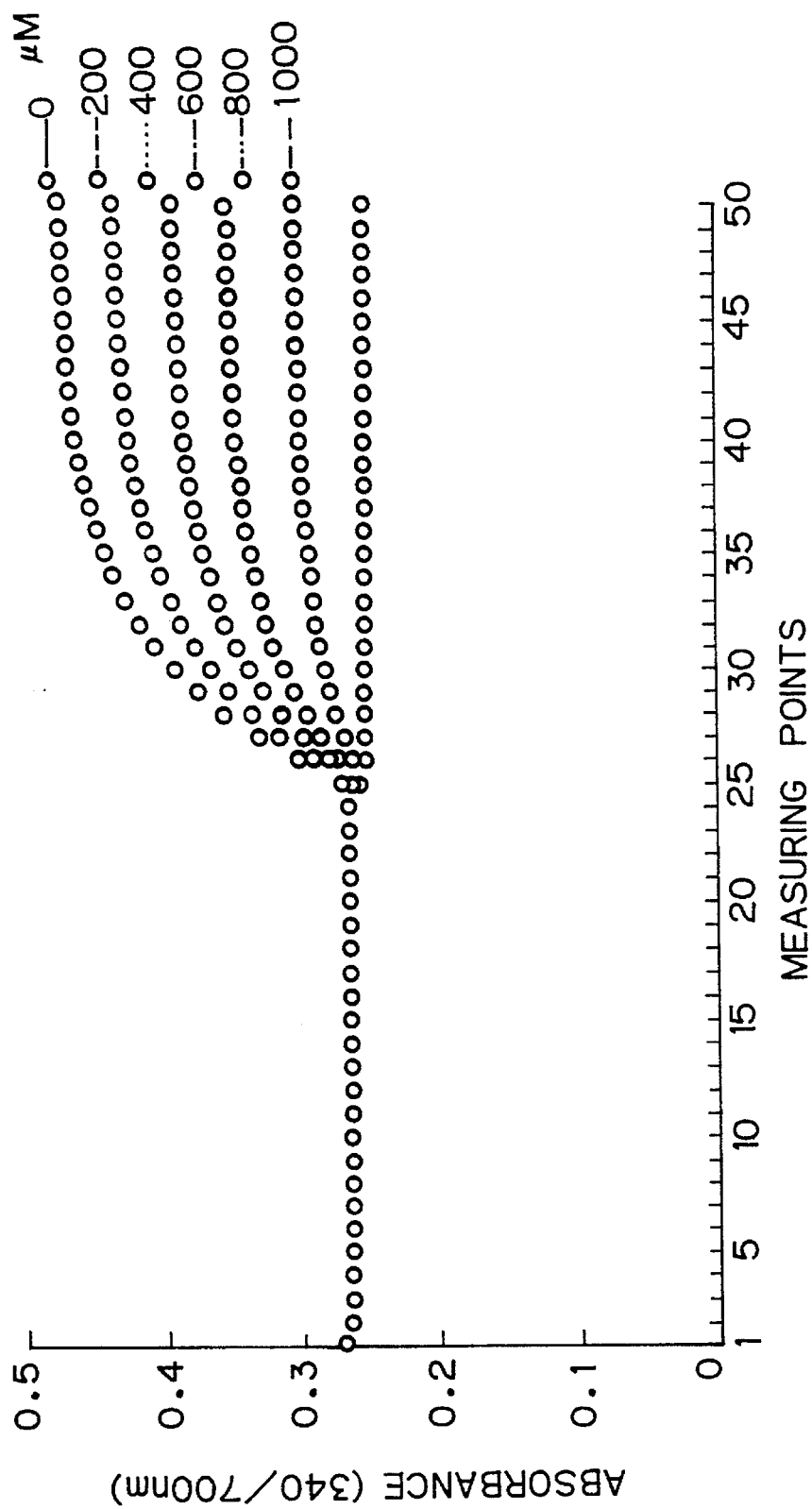
FIG. 4 is a graph showing reaction time courses in the calibration curve of 3-hydroxybutyric acid.

The reaction time courses of the calibration curves shown in Example 1 were shown in FIG. 3 (AcA) and FIG. 4 (3-HB). The transverse axes in the drawings show measuring points with the automatic analyzer, Hitachi Model 7150, and the ordinate axes show the absorbance at a primary wavelength of 340 nm and a secondary wavelength of 700 nm.

In FIG. 3, AcA in the sample is completely converted to 3-HB in the first step of the reaction with the acid of the action of 3-HBD in the presence of NADH which is controlled to a low concentration. Even when AcA at a high concentration is reacted, NADH consumed at this time is compensated to an initial level in a short time by the conjugation reaction with the isocitrate dehydrogenase which forms reduced-type nicotinamide adenine dinucleotide. In the second step of the reaction, the reaction for converting 3-HB to AcA is carried out by adding an excess amount of NAD and by shifting a pH to an alkaline region so that the reaction is completed in a short time such as 5 minutes.

In FIG. 4, 3-HB in the sample does not change at all in a first step of the reaction; the reaction for converting from 3-HB to AcA is carried out according to the second step of the reaction, the reaction is completed in a short time such as 5 minutes.

EXAMPLE 3

Addition and Recovery Test in the Assay of the Total Ketone Body

Patient blood serums containing various concentrations of the total ketone body, and samples prepared by adding known amounts of AcA and 3-HB therein were subjected to the method as in Example 1 under the assay conditions of Example 1, and the precision of assayed values under the present assayed conditions were examined on the basis of the recoveries of AcA and 3-HB added. The results are shown in Table 1 (AcA) and Table 2 (3-HB).

Mean recoveries were almost 100%, which show the precision of measured values under the measurement conditions of this invention.

TABLE 1

| Addition & Recovery Test (AcA) | | | | |
|---|---|---|---|---|
| Patient blood serum (μM) | Amount added (μM) | Theoretical value (μM) | Measured value (μM) | Recovery (%) |
| 30 | 83 | 113 | 109 | 96.5 |
|  | 170 | 200 | 199 | 99.5 |
| 122 | 83 | 205 | 214 | 104.3 |
|  | 170 | 292 | 286 | 97.9 |
| 202 | 83 | 285 | 281 | 98.6 |
|  | 170 | 372 | 371 | 99.7 |
|  |  |  | Mean | 99.4 |

TABLE 2

| Addition & Recovery Test (3-HB) | | | | |
|---|---|---|---|---|
| Patient blood serum (μM) | Amount added (μM) | Theoretical value (μM) | Measured value (μM) | Recovery (%) |
| 30 | 101 | 131 | 132 | 100.8 |
|  | 200 | 230 | 228 | 99.1 |
| 122 | 101 | 223 | 219 | 98.2 |
|  | 200 | 322 | 311 | 96.6 |
| 202 | 101 | 303 | 299 | 98.7 |
|  | 200 | 402 | 396 | 98.5 |
|  |  |  | Mean | 98.7 |

EXAMPLE 4

Precision in the Assay of the Total Ketone Body

With respect to the simultaneous reproducibility, the AcA measurement precision in the method of assaying the total ketone body according to the present invention was compared with a conventional absorbance damping method. Measurement conditions are as shown in Example 1.

As a conventional absorbance damping method, "Ketone Test A (Sanwa)" manufactured by Sanwa Kagaku Kenkyusho for measuring acetoacetic acid in blood was used according to the attached explanation, and measurement was carried out by means of the automatic analyzer, Hitachi Model 7150.

Pooled normal blood serums to which 50 µM, 100 µM and 200 µM of AcA were added respectively were used as samples, and the assay precision was compared in terms of coefficients of variation in, absorbance to be obtained by measuring the same specimen 10 times concurrently.

The results are shown in Table 3.

In comparison with the absorbance damping method, it was confirmed that the method of the present invention is remarkably precise.

TABLE 3

| | Simultaneous Reproducibility | | |
|---|---|---|---|
| | 50 µM AcA added serum | 100 µM AcA added serum | 200 µM AcA added serum |
| absorbance damping method | | | |
| n | 10 | 10 | 10 |
| Max. | 0.0200 | 0.0270 | 0.0491 |
| Min. | 0.0156 | 0.0238 | 0.0441 |
| S.D. | 0.00148 | 0.00104 | 0.00175 |
| Mean | 0.01778 | 0.02521 | 0.04591 |
| C.V. (%) | 8.32 | 4.13 | 3.81 |
| Method of the present invention | | | |
| n | 10 | 10 | 10 |
| Max. | 0.0575 | 0.0707 | 0.0929 |
| Min. | 0.0561 | 0.0675 | 0.0904 |
| S.D. | 0.00046 | 0.00093 | 0.00069 |
| Mean | 0.05703 | 0.06915 | 0.09202 |
| C.V. (%) | 0.81 | 1.34 | 0.75 |

EXAMPLE 5

Interference to Measured Values by the Lactate Acid Dehydrogenase in Samples

The absorbance of the pooled normal serum to which 5000 IU/l of lactate dehydrogenase and 2 mM of pyruvic acid or 20 mM of lactic acid were added were compared with the absorbance obtained by the measurement according to the present invention using the pooled serum with no additional component. The results are shown in Table 4. Measurement conditions are as in Example 1.

According to the method of the present invention, even if lactate dehydrogenase enzyme and as its substrate, pyruvic acid or lactic acid exist at a high concentration, no change was observed in the measured absorbance. This shows that their affection is completely avoided.

TABLE 4

| Interference to Measured Values by the Lactate Dehydrogenase in the Samples | | | |
|---|---|---|---|
| | Pooled serum with noting added | Lactate dehydrogenase and Pyruvic acid (2 mM) | Lactate dehydrogenase Lactic acid (20 mM) |
| Measured absorbance | 0.0477 | 0.0470 | 0.0464 |

EXAMPLE 6

Correlativity

The precision of the measured values of the total ketone body in the present invention was confirmed in terms of the correlativity with known methods. Known methods are as shown below.

1. AcA sample reagent (absorbance damping method)
    Manufacturer: Sanwa Kagaku Kenkyusho
    Trade name: "Ketone Test A (Sanwa)" for measuring acetoacetic acid in blood
2. 3-HB sample reagent (absorbance increasing method)
    Manufacturer: Sanwa Kagaku Kenkyusho
    Trade name: "Ketone Test B (Sanwa)" for measuring 3-hydroxybutyric acid in blood The method of the present invention was carried out under the conditions described in Example 1, and the measurement of the known methods was carried out by means of the automatic analyzer (Hitachi Model 7150) using each of the above reagents according to the attached explanation.

Figure 5:
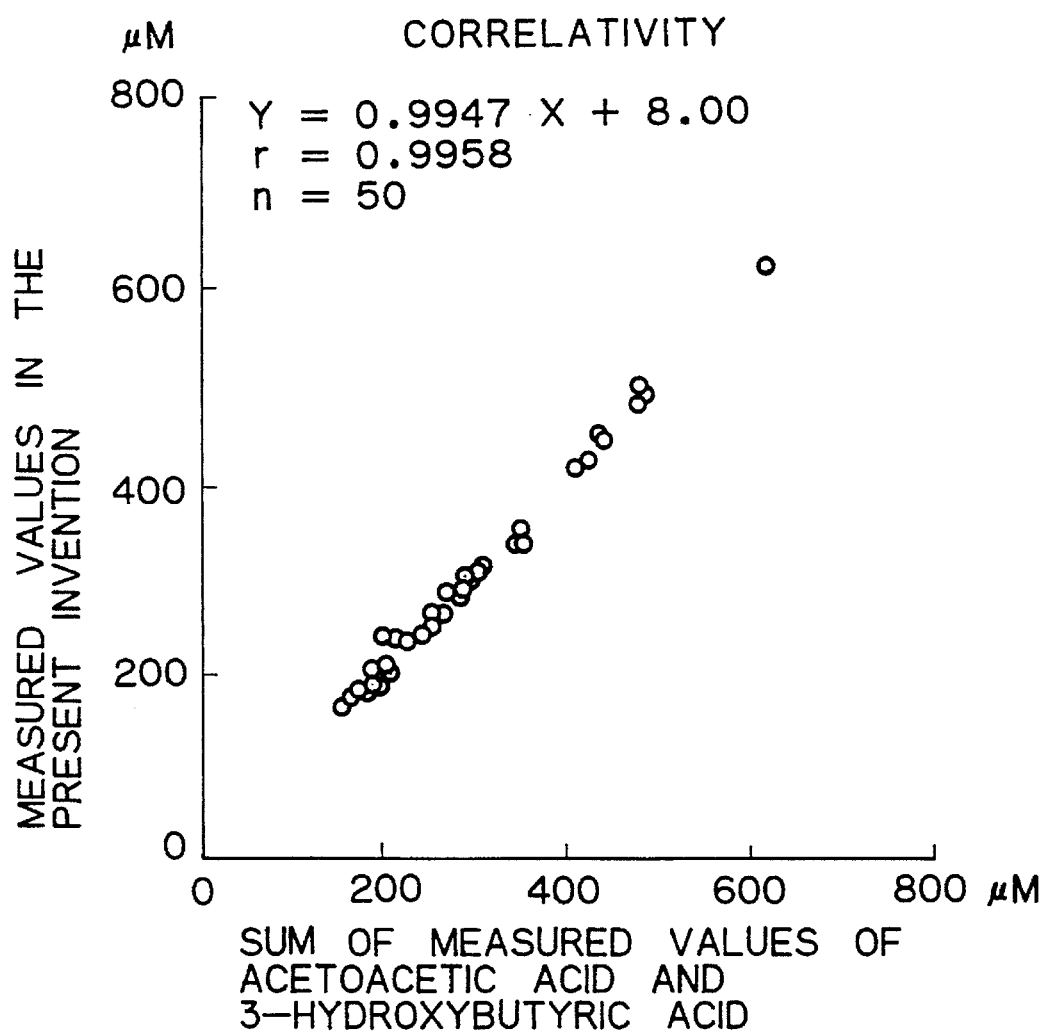
FIG. 5 is a graph showing the correlativity between the sum of the results of assay of "Ketone Test A "Sanwa"" and "Ketone Test B "Sanwa"" and the assayed values according to the present invention.

Correlativity between the sum of the results of the measurement according to "Ketone Test A (Sanwa)" and "Ketone Test B (Sanwa)" and the measured values in the present invention is shown in FIG. 5.

According to the results, nearly Y=X and the coefficient of correlation is nearly 1. It is revealed that the method of measurement according to the present invention has a high correlativity with the conventional methods and exhibits very high reliability.

EFFECTS OF THE INVENTION

As shown in the above Examples, the method of assay according to the present invention has an extremely high precision and can be easily applied to an automatic analyzer. Namely, according to the method of the present invention, the assay of the total ketone body, particularly AcA, which has been a problem, has become simple and highly precise. In addition, the assay having high reliability by means of an automatic analyzer has become possible without any pretreatment of samples.

What is claimed is:

1. A method of assaying the total ketone body in a sample, which is applicable to an automatic analyzer and comprises the steps of:

(1) converting acetoacetic acid in the sample to 3-hydroxybutyric acid with the aid of 3-hydroxybutyrate dehydrogenase in the presence of reduced-type nicotinamide adenine dinucleotide, said reaction being conjugated with another reaction in which the resulting oxidized-type nicotinamide adenine dinucleotide is used as a coenzyme to form its reduced-type;

(2) converting both 3-hydroxybutyric acid originally existed in the sample and 3-hydroxybutyric acid converted by step (1) to acetoacetic acid with the aid of 3-hydroxybutyrate dehydrogenase and oxide-type nicotinamide adenine dinucleotide; and (3) measuring the absorbance of reduced-type nicotinamide adenine dinucleotide formed by step (2).

2. A method according to claim 1 wherein said another enzyme reaction is carried out using an enzyme selected from the group consisting of isocitrate dehydrogenase, alcohol dehydrogenase, glucose-6-phosphate dehydrogenase, aldehyde dehydrogenase and glucose dehydrogenase, and with its substrate.

3. A method according to claim 2 wherein said enzyme is isocitrate dehydrogenase, and said substrate is citric acid.

4. A method according to claim 1 wherein in step (2), an excess amount of oxydized-type nicotinamide adenine dinucleotide is added to the reaction system, and the pH of the system is shifted to an alkaline region to convert both 3-hydroxybutyric acid originally existed in the sample and 3-hydroxybutyric acid previously converted from acetoacetic acid to acetoacetic acid.

5. A kit of reagent for assaying the total ketone body comprising:

(1) a buffering agent, (2) 3-hydroxybutyrate dehydrogenase, (3) reduced-type nicotinamide adenine dinucleotide, (4) oxidized-type nicotinamide adenine dinucleotide, (5) an enzyme capable of converting oxidized-nicotinamide adenine dinucleotide to reduced-type nicotinamide adenine dinucleotide with the conjugated reaction with 3-hydroxybutyrate dehydrogenase, and (6) a substrate of the enzyme of the above (5).

6. A kit of reagent according to claim 5 further comprising an inhibitor of the enzyme of (5).

* * * * *